(12) United States Patent
Hunke et al.

(10) Patent No.: US 8,696,868 B2
(45) Date of Patent: Apr. 15, 2014

(54) DISULFO-TYPE FLUORESCENT WHITENING AGENT COMPOSITIONS

(75) Inventors: Bernhard Hunke, Hennef (DE); Andrei Tauber, Cologne (DE); Michael Kraemer, Kuerten (DE); Guenter Klug, Langenfeld (DE)

(73) Assignee: Blankophor GmbH & Co. KG (DE)

( * ) Notice: Subject to any disclaimer, the term of this patent is extended or adjusted under 35 U.S.C. 154(b) by 0 days.

(21) Appl. No.: 13/496,682

(22) PCT Filed: Sep. 17, 2010

(86) PCT No.: PCT/EP2010/063702
§ 371 (c)(1),
(2), (4) Date: Apr. 23, 2012

(87) PCT Pub. No.: WO2011/033064
PCT Pub. Date: Mar. 24, 2011

(65) Prior Publication Data
US 2012/0199302 A1    Aug. 9, 2012

(30) Foreign Application Priority Data

Sep. 17, 2009   (EP) .................................... 09170579

(51) Int. Cl.
*D21F 11/00*    (2006.01)
(52) U.S. Cl.
USPC ....................................................... 162/158
(58) Field of Classification Search
USPC ........ 162/158; 252/301.23; 8/648; 544/193.2
See application file for complete search history.

(56) References Cited

U.S. PATENT DOCUMENTS

| 6,143,889 | A  | * | 11/2000 | Metzger et al. | ............ 544/193.2 |
| 6,210,449 | B1 | * | 4/2001  | Rohringer et al. | ................ 8/648 |
| 6,723,846 | B1 | * | 4/2004  | Metzger et al. | ............ 544/193.2 |
| 2008/0073617 | A1 | * | 3/2008 | Cockcroft et al. | ....... 252/301.23 |
| 2008/0191169 | A1 | * | 8/2008 | Rohringer et al. | ....... 252/301.25 |

FOREIGN PATENT DOCUMENTS

| EP | 1752453 A | 2/2007 |
| EP | 09170579.8 | 9/2009 |
| WO | 9842685 | 10/1998 |
| WO | 0119804 | 3/2001 |
| WO | 2011033064 | 3/2001 |
| WO | 02055646 | 7/2002 |
| WO | 2006045714 | 5/2006 |

OTHER PUBLICATIONS

Notification Concerning the Transmittal of the Preliminary Report on Patentability issued in International Application No. PCT/EP2010/063702 dated Mar. 29, 2012; 8 pages.
International Search Report and Written Opinion issued in International Application No. PCT/EP2010/063702 dated May 12, 2011; 10 pages.

* cited by examiner

*Primary Examiner* — Mark Halpern
(74) *Attorney, Agent, or Firm* — Cantor Colburn LLP

(57) ABSTRACT

Fluorescent whitening agent compositions include at least two specific disulfo-type fluorescent whitening agents for optically whitening paper or board.

7 Claims, 1 Drawing Sheet

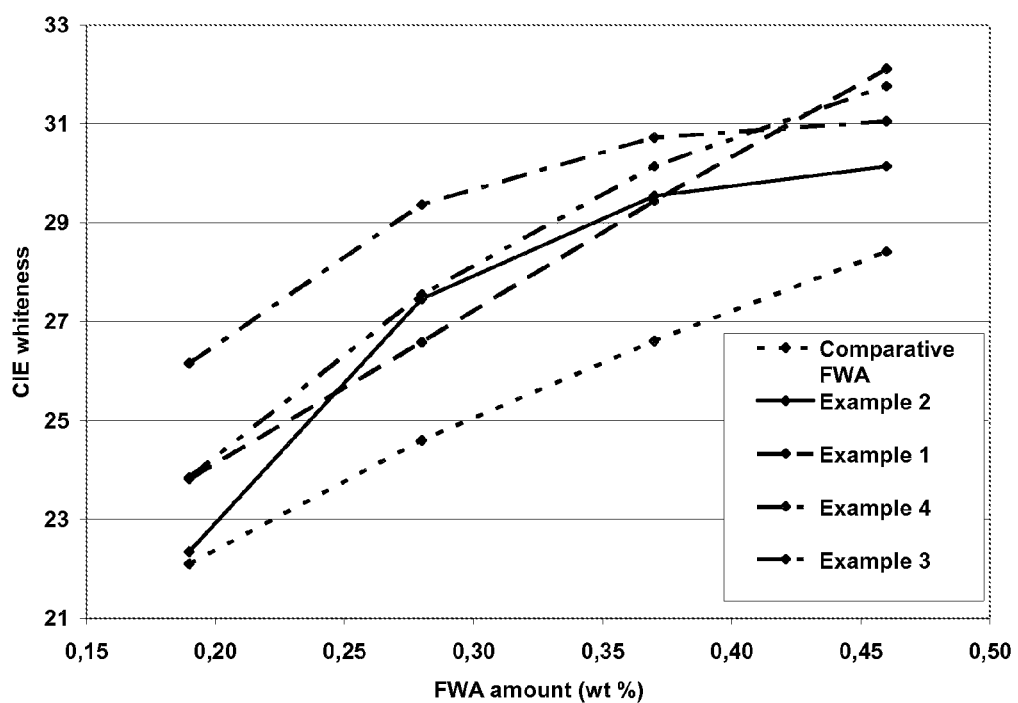

DISULFO-TYPE FLUORESCENT WHITENING AGENT COMPOSITIONS

This application is a 371 of PCT/EP2010/063702 filed Sep. 17, 2010. Priority under 35 U.S.C. §119(a) and 35 U.S.C. §365(b) is claimed from European Patent Application No. 09170579.8, filed on Sep. 17, 2009, the disclosure of which is also incorporated herein by reference.

BACKGROUND

The present disclosure relates to fluorescent whitening agent compositions containing at least two specific disulfo-type fluorescent whitening agents for whitening paper or board.

It is well known that the whiteness of paper and board can be improved by the addition of fluorescent whitening agents (FWAs). The most important fluorescent whitening agents used in the paper and board industry are anilino-substituted bistriazinyl derivatives of 4,4'-diaminostilbene-2,2'-disulfonic acid (flavonic acid). From these fluorescent whitening agents disulfo-, tetrasulfo- and hexasulfo-types are known. The disulfo-type fluorescent whitening agents with no sulfonic acid groups at the aniline rings have a low solubility in water and a high affinity for cellulose fibres. They are especially suitable for use at the wet-end of paper making process. The hexasulfo-type fluorescent whitening agents with two sulfonic acid groups at each aniline ring have a high solubility in water and a low affinity for cellulose fibres. They are more specialty products when very high whiteness is desired. The tetrasulfo-type fluorescent whitening agents with one sulfonic acid group at each aniline ring exhibit a behaviour between the disulfo- and hexasulfo-type fluorescent whitening agents and are most commonly used for whitening paper or board.

For ease of handling and metering, the paper and board industry demands fluorescent whitening agents to be supplied in a liquid form, preferably as a concentrated aqueous solution, which should be stable to prolonged storage over a wide temperature range. Due to the low solubility of disulfo-type fluorescent whitening agents in water, currently solubilising auxiliaries such as urea, triethanolamine or diethylene glycol are added in amounts of up to 30% to provide storage stability for concentrated aqueous solutions of disulfo-type fluorescent whitening agents. These solubilising agents have no affinity to cellulose and contaminate the effluent from the paper mill, thus being undesired. EP-A-1 752 453 teaches storage stable solutions of disulfo-type fluorescent whitening agents which contain specific counter-ions for the sulfonic acid groups, which counter-ions are derived from specific aminoalkanols. WO 02/055646 A1 discloses concentrated aqueous solutions containing a mixture of two specific disulfo-type fluorescent whitening agents.

Alternatively, slurries or dispersions of disulfo-type fluorescent whitening agents in water are known, e.g. from EP 0 884 312 B1. However, in order to enable the metering of homogenous preparations into the papermaking process, usually stirring is required.

BRIEF SUMMARY

Surprisingly, it has been found that problems of the prior art can be overcome by using mixtures or combinations of specific disulfo-type fluorescent whitening agents having carboxylic acid groups at the aniline rings. These mixtures, when used for whitening paper or board, yield paper or board of improved whiteness. Further, the disulfo-type fluorescent whitening agents used enable stable concentrated aqueous preparations or solutions to be formed, without addition of solubilising auxiliaries. Moreover, the production process of those fluorescent whitening agents is more cost-effective, compared to that of the commonly used disulfo-type fluorescent whitening agents, since it dispenses with laborious isolation and filtration steps.

Therefore, the present invention relates to fluorescent whitening agent (FWA) compositions suitable for optically whitening paper or board, wherein the composition contains at least two fluorescent whitening agents selected from the fluorescent whitening agents of formula (1), formula (2) and formula (3)

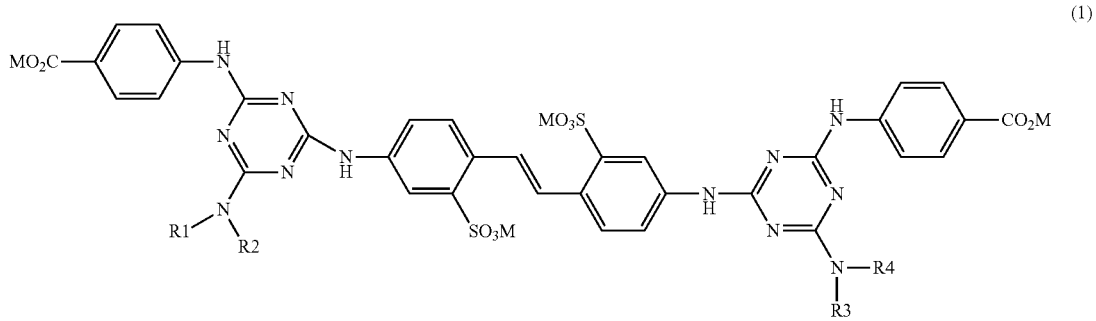

(1)

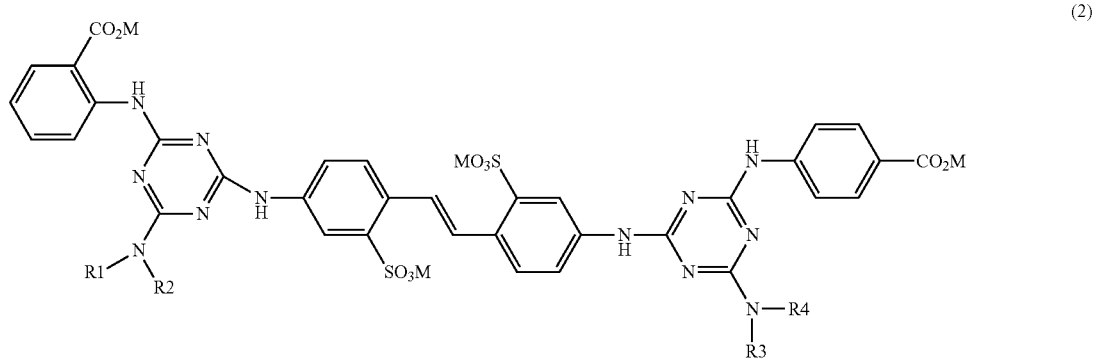

(2)

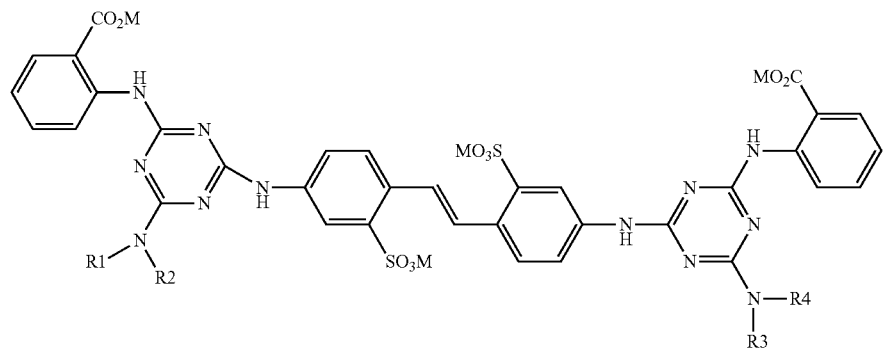

wherein $R_1$, $R_2$, $R_3$ and $R_4$ represent, independently of each other, hydrogen, cyano, $C_1$-$C_4$ alkyl, $C_2$-$C_4$ cyanoalkyl, $C_2$-$C_4$ hydroxyalkyl, or $C_1$-$C_4$ alkoxyalkyl; or $R_1$ and $R_2$ or $R_3$ and $R_4$ independently of each other together with N atom form morpholine, piperidine or pyrrolidine ring; or —$(CH_2)_1$—$SO_3M$, where 1 is 1, 2 or 3; or —$(CH_2)_i$—COOR, —$(CH_2)_i$—CONHR, —$(CH_2)_i$—OR, where i is an integer from 1 to 4, R is $C_1$-$C_3$ alkyl or has the same meaning as M;

M represents hydrogen, or one equivalent of a cation, in particular Li, Na, K, Ca, Mg, ammonium, or ammonium which is mono-, di-, tri- or tetra-substituted by $C_1$-$C_4$ alkyl or $C_2$-$C_4$ hydroxyalkyl.

The invention also refers to a process for preparing the fluorescent whitening agent (FWA) compositions, and their use for whitening paper in the pulp or at the surface, e. g. in coating or size press applications. Further, the invention relates to a process for whitening paper and to paper obtainable by that process. Preferred embodiments of the invention are described in the description hereinafter, the FIGURE and the claims.

BRIEF DESCRIPTION OF THE DRAWINGS

FIG. 1 is a diagram showing the whitening performance of different fluorescent whitening agents and mixtures thereof

DETAILED DESCRIPTION OF INVENTION

In one embodiment of the disclosure, the fluorescent whitening agent composition is a wet-end composition, and the process is a process for whitening paper, wherein a pulp or pulp suspension is brought into contact with said composition. In another embodiment, the fluorescent whitening agent composition is used for preparing a size press liquor or a coating composition.

According to the disclosure, the composition or mixture contains at least two of the bis-triazinylamino-stilbene compounds of the above defined formulae (1), (2) and (3). In the context of the disclosure, in the formulae (1), (2) and (3) the alkyl group can be linear or branched, and the possible substituents of the alkyl group, which are alkoxy, cyano, and/or hydroxyl groups, can be attached at any position of the alkyl chain. In the present disclosure, $C_1$-$C_4$ alkoxyalkyl means $C_1$-$C_4$ alkyl substituted with $C_1$-$C_4$ alkoxy. In a preferred embodiment, $R_1$, $R_2$, $R_3$ and $R_4$ represent, independently of each other, $C_2$-$C_4$ hydroxyalkyl, $C_1$-$C_4$ alkoxyalkyl or $C_1$-$C_4$ alkyl, preferably $C_2$-$C_4$ hydroxyalkyl or $C_1$-$C_4$ alkoxyalkyl, and in other embodiments, hydroxyethyl or hydroxyisopropyl. Most particularly, $R_1$, $R_2$, $R_3$ and $R_4$ can represent hydroxyethyl.

M can be hydrogen, Na, K, Ca, or Mg, in other embodiments, M is Na, K or hydrogen, and in still other embodiments, M is Na.

The fluorescent whitening agents of formulae (1), (2) and (3) and the mixtures thereof can be prepared by known procedures. The fluorescent whitening agents are used as free acids or as salts thereof, e.g., alkali metal salts. Generally, the compounds are prepared by reacting cyanuric chloride with 4,4'-diaminostilbene-2,2'-disulfonic acid or a salt thereof, 2-aminobenzoic acid and/or 4-aminobenzoic acid, and substituted aliphatic amines or heterocyclic compounds. The ratio of 2-aminobenzoic acid to 4-aminobenzoic acid can be selected such that a desired ratio of the fluorescent whitening agents of formulae (1), (2) and/or (3) is obtained in the mixture. Exemplary processes are shown in Examples 3 and 4 described below. PL patent 61710 discloses the preparation of some specific fluorescent whitening agents of the above defined formulae with one carboxylic acid group in p-position of each aniline ring. GDR (DDR) patent 55 668 discloses a further process for preparing some specific fluorescent whitening agents of the above defined formulae. The purification of the fluorescent whitening agents of formulae (1), (2) and (3) is easier and thus more cost-effective than for commonly used disulfo-type fluorescent whitening agents, since isolation steps can be avoided. The purification could be carried out by, for example, membrane filtration. In contrast to the water evaporation or salt precipitation steps disclosed in PL patent 61710, the purification of the fluorescent whitening agents can be achieved by membrane filtration and the product obtained can be used as such. This is due to the surprisingly higher solubility of the fluorescent whitening agents.

The composition of the fluorescent whitening agents of formulae (1), (2) and/or (3) can be produced in form of a mixture with the desired ratio of the fluorescent whitening agents. Suitable processes are described in the Examples below. Alternatively, the composition can be produced by preparing separately the fluorescent whitening agents of formulae (1), (2) and/or (3) by the methods known in the art and as described above, and then blending or mixing together in the desired ratio after their preparation.

The composition of the disclosure contains at least two or more, and in one embodiment two or three, fluorescent whitening agents selected from the fluorescent whitening agents of the formulae (1), (2) and (3). In one embodiment, the composition comprises the fluorescent whitening agents of the formulae (1) and (2). In another embodiment, the composition comprises the fluorescent whitening agents of the formulae (1) and (3). In a further embodiment, the composition comprises the fluorescent whitening agents of the formulae (2) and (3). In yet another embodiment, the composition comprises the fluorescent whitening agents of the formulae (1), (2) and (3). The composition can also contain one or more of each of a fluorescent whitening agent of the formulae (1), (2) and/or (3). In addition, the composition can contain one or more known bis-triazinylamino-stilbene or distyryl-biphenyl based fluorescent whitening agents.

The amounts of the fluorescent whitening agents present in the composition depends on the number of fluorescent whitening agents present and which fluorescent whitening agents are present. According to one embodiment, the composition contains preferably at least one fluorescent whitening agent of formula (1) in an amount of 0 to 99 weight-%, and in other embodiments, 2 to 90 weight-%, and in still other embodiments 5 to 80 weight-%; at least one fluorescent whitening agent of formula (2) in an amount of 0 to 99 weight-%, in other embodiments 2 to 90 weight-%, most in still other embodiments 5 to 80 weight-%; and at least one fluorescent whitening agent of formula (3) in an amount of 0 to 99 weight-%, in other embodiments 2 to 90 weight-%, and in still other embodiments 5 to 80 weight-%; in each case based on 100 weight-% of the total amount of the present fluorescent whitening agents of the formulae (1), (2) and/or (3). In further embodiments, the composition contains at least one fluorescent whitening agent of formula (1) in an amount of 10 to 80 weight-%, and in other embodiments 20 to 70 weight-%, at least one fluorescent whitening agent of formula (2) in an amount of 10 to 60 weight-%, and in other embodiments 10 to 50 weight-%, and at least one fluorescent whitening agent of formula (3) in an amount of 10 to 80 weight-%, and in other embodiments 20 to 70 weight-%, in each case based on 100 weight-% of the total amount of the present fluorescent whitening agents of the formulae (1), (2) and/or (3).

The fluorescent whitening agent composition can be present in liquid form, in particular as a solution, or in form of a powder. In some embodiments, the compositions contain water, in particular in an amount of 20 to 90 weight-%, based on 100 weight-% of the total amount of the fluorescent whitening agents and water. Such aqueous fluorescent whitening agent compositions or mixtures are present in liquid form, in particular as a solution. In one embodiment, those are free of crystalline whitener particles, in particular their hydrate forms.

The fluorescent whitening agent compositions, in particular the aqueous compositions, may contain a small amount of auxiliaries. This might be particularly relevant for fluorescent whitening agent compositions used in cold regions to enhance preparations' cold stability. In one embodiment, the aqueous fluorescent whitening agent composition contains less than 30% by weight, in other embodiments less than 20% by weight, in still other embodiments less than 15% by weight, and in yet still other embodiments less than 10% by weight of components other than the fluorescent whitening agents and water, for example, formulation auxiliaries, such as standardizing agents, surface-active compositions, antifoams, organic thickeners, preservatives, and/or electrolytes may be used. However, for ecological reasons, the aqueous fluorescent whitening agent preparation preferably contains only very small amounts of other components, e.g. organic additives or auxiliaries, particularly altogether less than 3% by weight in most embodiments, and in particular less than 1% by weight in other embodiments, based on 100% by weight of the aqueous fluorescent whitening agent composition. The composition may contain no organic co-solvents, and/or urea. In a further embodiment, the composition consists or consists essentially of the fluorescent whitening agents and water.

The aqueous fluorescent whitening agent composition can be prepared by introducing the fluorescent whitening agents of formulae (1), (2) and/or (3) or their mixture in the desired ratio in form of a powder or a concentrated solution thereof into water. Any auxiliaries can optionally be added during or after preparation of the mixture.

The composition according to the disclosure can be used for whitening paper or board, preferably in the pulp suspension (stock) or pulp, in particular in the wet-end. Alternatively, the composition can be used for whitening paper at the surface. In wet-end applications the compositions can be added at any point of the pulp circuit, e.g. chests or pipes, before sheet forming. Depending on the papermaking process used, the compositions can be added to the papermaking process also in diluted form, wherein the composition has been diluted to a desired concentration by addition of water and/or auxiliaries. In one embodiment, the aqueous, fluorescent whitening agent composition is introduced, optionally after dilution with water, to the pulp or pulp suspension. The compositions can be added continuously or discontinuously. The application is beneficial for both wood-containing pulps and wood-free pulps, in particular for wood-containing pulps. In surface application, the compositions can be used for preparing size press liquors or coating slips.

The aqueous fluorescent whitening agent compositions exhibit high storage stability and ease of application. Simultaneously, they provide high affinity (substantivity) to fibres and high whitening performance.

The disclosure also refers to a process for whitening paper, which comprises providing a pulp or pulp suspension; adding a fluorescent whitening agent composition as described above to the pulp or pulp suspension, in an amount of 0.01 to 5% by weight, and in other embodiments 0.02 to 2% by weight, based on 100% by weight of dry pulp; producing a paper sheet from the pulp; and drying the sheet. In one embodiment of this process, the composition is added, after dilution with water and/or auxiliaries, in particular dilution with water, to the pulp or pulp suspension.

Paper produced by using the fluorescent whitening agent compositions according to the invention exhibits higher whiteness compared to paper produced using the typically used disulfo-type fluorescent whitening agents.

The whiteness of the papers produced can be characterized by the CIE whiteness. Different fluorescent whitening agents can be compared to each other with respect to the saturation behaviour when determined according to CIE whiteness. In other words, if a larger amount of fluorescent whitening agent is used and no further increase in whiteness is found, there is saturation behaviour and there may even be adverse effects on the whiteness when using higher amounts. The effect of saturation is also referred to as greening. The greening limit, i.e. the point at which increasing amounts of fluorescent whitening agent used results in virtually no further increase in whiteness, can be derived, for example, from the a*-b* diagram, where a* and b* are the colour coordinates in the CIE-L*a*b* system.

The following examples illustrate the invention and show preferred embodiments without limiting the scope of protection.

EXAMPLES

Example 1

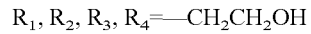

Step 1: Reaction of cyanuric chloride with 2,2'-disulfo-4,4'-stilbenediamine disodium salt A two-liter flask equipped with an agitator, pH electrode, thermometer and condenser was charged with 600 ml of water at 8° C., and 100 g (0.542 mol) cyanuric chloride. After pH was decreased to 4.5, a solution of 112.2 g (0.27 mol) of 2,2'-disulfo-4,4'-stilbenediamine disodium salt in 835 g water was added dropwise. At the same time 10% (w/w) solution of sodium hydroxide (222 g) was added dropwise to the reaction mixture to keep the pH at 4.5 while the mixture was heated up to 16° C. After addition of the reagents the reaction mixture was stirred at 16° C. for 1 hour while the pH was maintained at 4.5.

Step 2: Reaction of Step 1 Intermediate with 4-Aminobenzoic Acid 296.1 g of 25% (w/w) solution of 4-aminobenzoic acid (0.54 mol) were added to the water suspension from step 1 in 45 min. The pH was kept constant (pH=6.8) by the simultaneous addition of 10% sodium hydroxide solution while temperature was gradually increased up to 60° C. The reaction mixture was then stirred at 60° C. and pH 6.8 until the consumption of the sodium hydroxide solution had stopped.

Step 3: Reaction of the Step 2 Intermediate with Diethanolamine 67.8 g (0.54 mol) of diethanolamine were added to the water suspension from step 2 in 20 minutes. The pH was kept constant (pH=8) by the simultaneous addition of 10% sodium hydroxide solution while temperature was gradually increased up to 100° C. The reaction mixture was then stirred at 100° C. and pH 8 for 3 hours. The resulting solution was cooled down to about 50° C. and clarified by filtration to yield the solution of a compound of the formula 1 (88.7%) as shown below.

Example 2

$R_1, R_2, R_3, R_4$=—$CH_2CH_2OH$

Step 1: Conditions are Identical with Those from Step 1 of Example 1

Step 2: Reaction of Step 1 Intermediate with 2-Aminobenzoic Acid 296.1 g of 25% (w/w) solution of 2-aminobenzoic acid (0.54 mol) were added to the water suspension from step 1 in 45 min. The pH was kept constant (pH=6.8) by the simultaneous addition of 10% sodium hydroxide solution while temperature was gradually increased up to 60° C. The reaction mixture was then stirred at 60° C. and pH 6.8 until the consumption of the sodium hydroxide solution had stopped.

Step 3: Reaction of the Step 2 Intermediate with Diethanolamine 67.8 g (0.54 mol) of diethanolamine were added to the water suspension from step 2 in 20 minutes. The pH was kept constant (pH=8) by the simultaneous addition of 10% sodium hydroxide solution while temperature was gradually increased up to 100° C. The reaction mixture was then stirred at 100° C. and pH 8 for 3 hours. The resulting solution was cooled down to about 50° C. and clarified by filtration to yield the solution of a compound of the formula 3 (89.4%) as shown below.

Example 3

$R_1, R_2, R_3, R_4$=—$CH_2CH_2OH$

Step 1: Conditions were Identical with Those from Step 1 of Example 1

Step 2: Reaction of step 1 intermediate with mixture of 4-aminobenzoic and 2-aminobenzoic acids (4/1, w/w)

296.1 g (0.54 mol) of a mixture of 4-aminobenzoic and 2-aminobenzoic acids (4/1, w/w) were added as 25% (w/w) solution to the water suspension from step 1 in 45 min. The pH was kept constant (pH=6.8) by the simultaneous addition of 10% sodium hydroxide solution while temperature was gradually increased up to 60° C. The reaction mixture was then stirred at 60° C. and pH 6.8 until the consumption of the sodium hydroxide solution had stopped.

Step 3: Reaction of the step 2 intermediate with diethanolamine 67.8 g (0.54 mol) of diethanolamine were added to the water suspension from step 2 in 20 minutes. The pH was kept constant (pH=8) by the simultaneous addition of 10% sodium hydroxide solution while temperature was gradually increased up to 100° C. The reaction mixture was then stirred at 100° C. and pH 8 for 3 hours. The resulting solution was cooled down to ca. 50° C. and clarified by filtration to yield the solution of a mixture of the compounds 1 (65%), 2 (30.3%) and 3 (4.7%) as shown below in an overall yield of 84.3%.

Example 4

$R_1, R_2, R_3, R_4$=—$CH_2CH_2OH$

Step 1: Conditions were Identical with Those from Step 1 of Example 1

Step 2: Reaction of step 1 intermediate with mixture of 4-aminobenzoic and 2-aminobenzoic acids (1/1, w/w)

296.1 g (0.54 mol) of a mixture of 4-aminobenzoic and 2-aminobenzoic acids (1/1, w/w) were added as 25% (w/w) solution to the water suspension from step 1 in 45 min. The pH was kept constant (pH=6.8) by the simultaneous addition of 10% sodium hydroxide solution while temperature was gradually increased up to 60° C. The reaction mixture was then stirred at 60° C. and pH 6.8 until the consumption of the sodium hydroxide solution had stopped.

Step 3: Reaction of the Step 2 Intermediate with Diethanolamine 67.8 g (0.54 mol) of diethanolamine were added to the water suspension from step 2 in 20 minutes. The pH was kept constant (pH=8) by the simultaneous addition of 10% sodium hydroxide solution while temperature was gradually increased up to 100° C. The reaction mixture was then stirred at 100° C. and pH 8 for 3 hours. The resulting solution was cooled down to ca. 50° C. and clarified by filtration to yield the solution of a mixture of the compounds 1 (25.9%), 2 (48.1%) and 3 (26%) as shown below in an overall yield of 92.6%.

The fluorescent whitening agents as shown below were obtained. The Comparative FWA shown below was used in the Application Example.

Comparative FWA
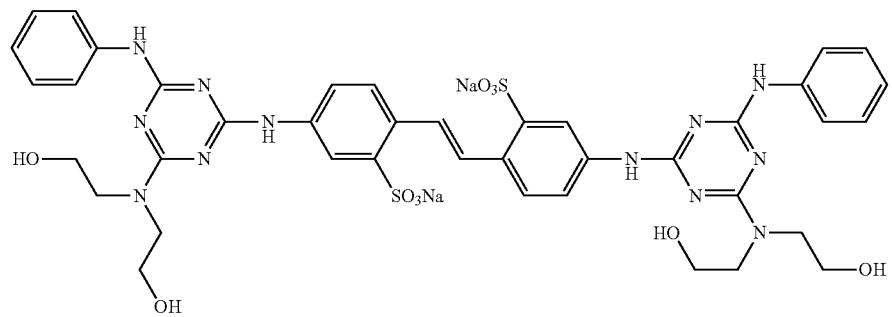
Example 1
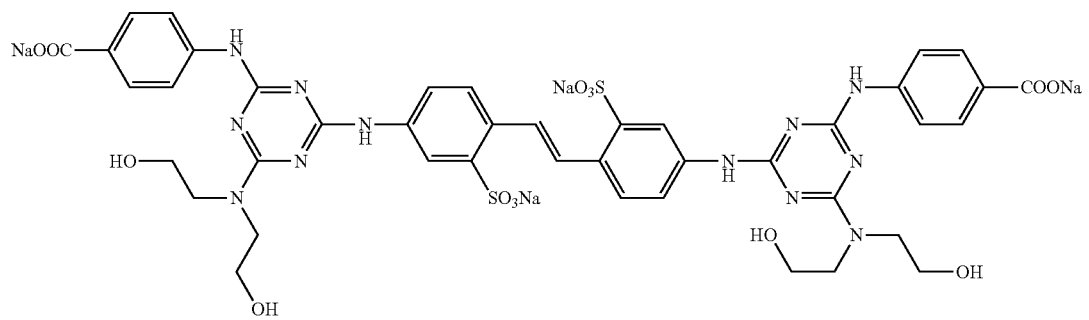
Example 2
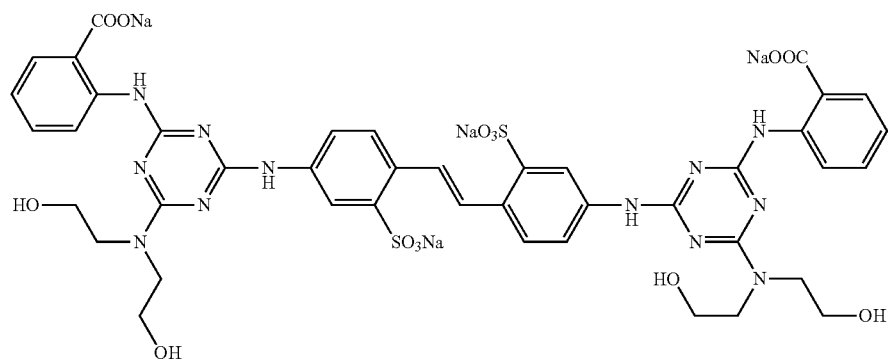
Example 3
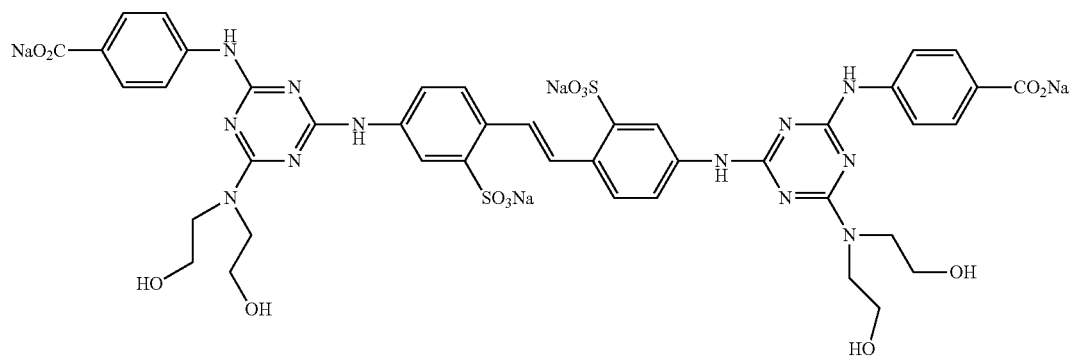
(65.0%)

-continued
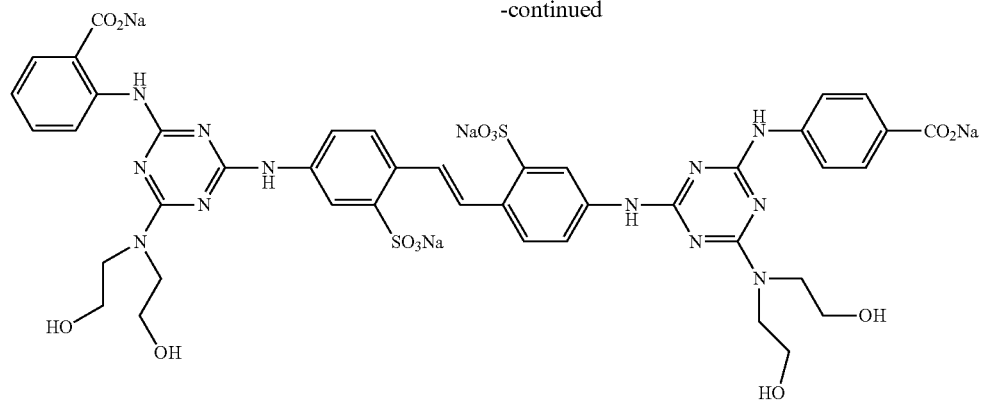
(30.3%)
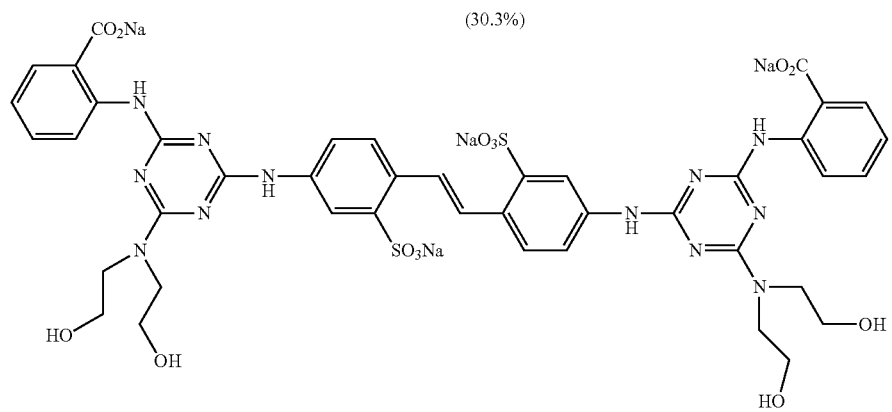
(4.7%)
Example 4
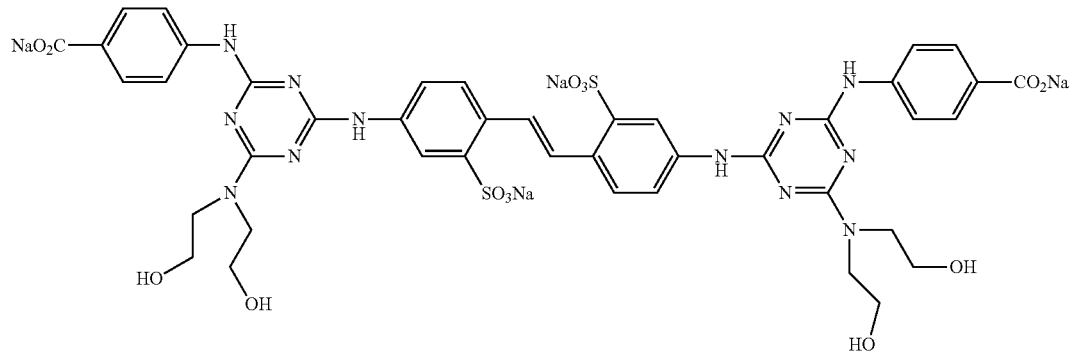
(25.9%)
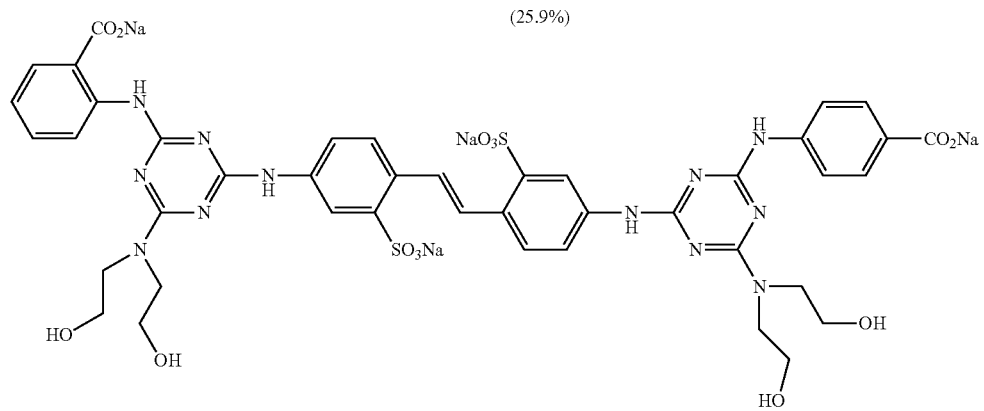
(48.1%)

-continued

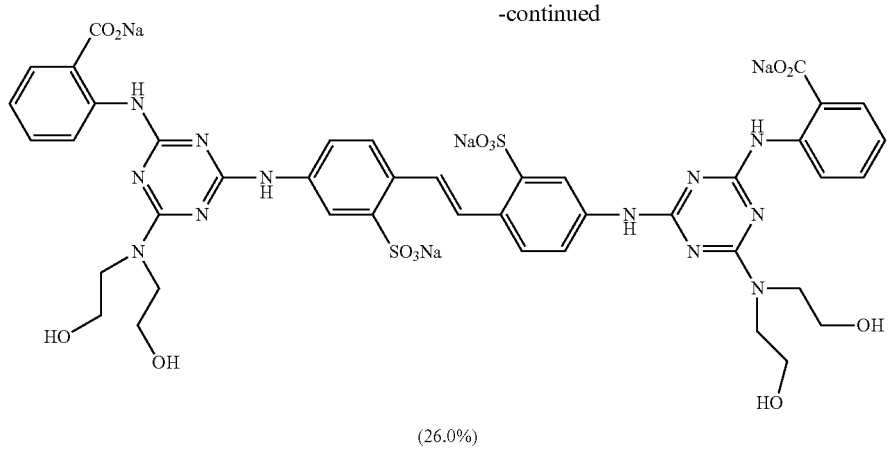

(26.0%)

These fluorescent whitening agents and mixtures were used in the following application example.

Application Example

The whitening performance of the fluorescent whitening agents and mixtures thereof was studied using the following test procedure.

The furnish (pulp suspension) was composed of 85 pts (parts, based on weight) of mechanical pulp and 15 pts of long fibres with a grinding degree of 40° SR (Schopper-Riegler).

800 ml of a 0.625% of corresponding furnish were weighted in a beaker to prepare a 5 g hand sheet of ~120 g/m² for each experimental series. A 0.1 wt % fluorescent whitening agent solution was prepared using distilled water. The amounts of fluorescent whitening agent as indicated in Table 1 below were achieved by adding a corresponding amount of the 0.1 wt % fluorescent whitening agent solution by a pipette to the stirred pulp suspension which was allowed to stir for 10 minutes after fluorescent whitening agent addition. The amounts of fluorescent whitening agent in Table 1 are calculated as active ingredient based on 100 wt % of dry pulp.

A wet filter paper was positioned on the wire of the sheet former, the stock is put on the sheet former and sucked dry. The formed hand sheet was protected by an additional dry filter, pressed and dried on a calender at 100° C. Thereafter, the obtained hand sheets were equilibrated in a climate room under standard conditions overnight and then measured with a Datacolor spectrometer (ISO2469) by determining CIE, L*, a* and b*, the light source used based on ISO2469 standard.

The results obtained are summarized in Table 1 and further shown in FIG. 1.

TABLE 1

| FWA | Amount (wt %) FWA | CIE whiteness | L* | a* | b* |
|---|---|---|---|---|---|
| Example 1 | 0.19 | 23.81 | 91.87 | 0.01 | 12.12 |
|  | 0.28 | 26.58 | 91.96 | 0.05 | 11.58 |
|  | 0.37 | 29.43 | 92.05 | 0.07 | 11.03 |
|  | 0.46 | 32.11 | 92.20 | 0.04 | 10.30 |
| Example 2 | 0.19 | 22.34 | 91.85 | −0.04 | 12.43 |
|  | 0.28 | 27.45 | 92.02 | 0.03 | 11.43 |
|  | 0.37 | 29.54 | 92.04 | 0.02 | 11.18 |
|  | 0.46 | 30.14 | 92.10 | 0.01 | 10.90 |
| Example 3 | 0.19 | 23.84 | 91.87 | 0.02 | 12.12 |
|  | 0.28 | 27.54 | 91.99 | 0.07 | 11.40 |
|  | 0.37 | 30.14 | 92.05 | 0.10 | 10.88 |
|  | 0.46 | 31.76 | 92.09 | 0.08 | 10.55 |
| Example 4 | 0.19 | 26.15 | 92.03 | 0.04 | 11.72 |
|  | 0.28 | 29.36 | 92.09 | 0.10 | 11.07 |
|  | 0.37 | 30.72 | 92.06 | 0.09 | 10.97 |
|  | 0.46 | 31.05 | 92.03 | 0.10 | 10.67 |

TABLE 1-continued

| FWA | Amount (wt %) FWA | CIE whiteness | L* | a* | b* |
|---|---|---|---|---|---|
| Comparative FWA | 0.19 | 22.09 | 91.85 | −0.05 | 12.48 |
|  | 0.28 | 24.59 | 91.91 | 0.03 | 11.98 |
|  | 0.37 | 26.60 | 91.96 | 0.06 | 11.69 |
|  | 0.46 | 28.41 | 92.05 | 0.08 | 11.25 |

Thus, the fluorescent whitening agent compositions according to the invention exhibit better whitening performance than the individual disulfo-type fluorescent whitening agents.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A fluorescent whitening agent composition for optically whitening paper or board, comprising:
at least two fluorescent whitening agents selected from the group of fluorescent whitening agents consisting of formula (1), formula (2) and formula (3)

(1)

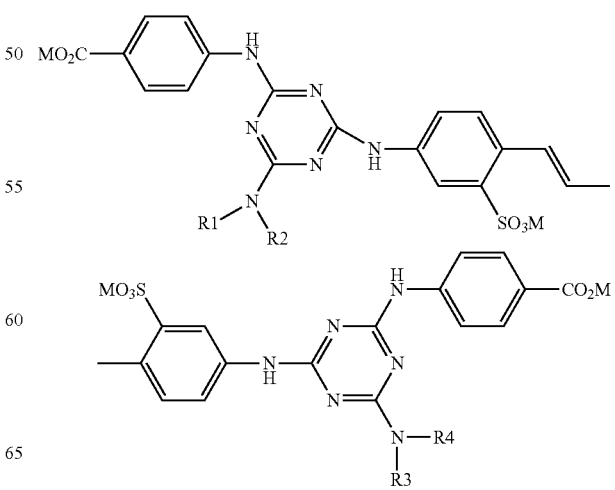

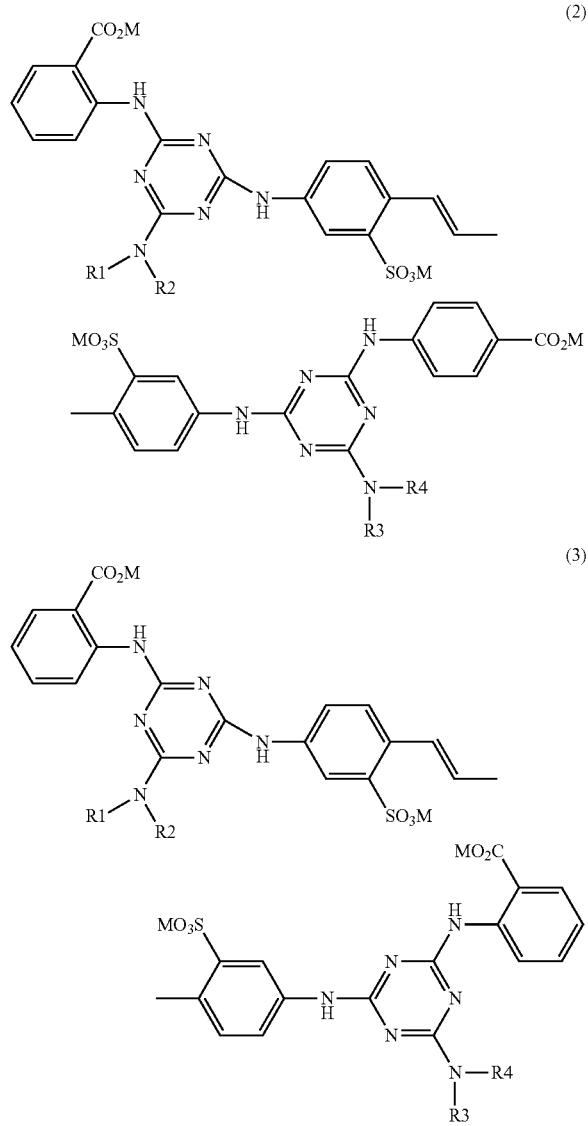

wherein $R_1, R_2, R_3$ and $R_4$ represent, independently of each other, hydrogen, cyano, $C_1$-$C_4$ alkyl, $C_2$-$C_4$ cyanoalkyl, $C_2$-$C_4$ hydroxyalkyl, or $C_1$-$C_4$ alkoxyalkyl; or $R_1$ and $R_2$ or $R_3$ and $R_4$ independently of each other together with a N atom form amorpholine, a piperidine or a pyrrolidine ring; or —$(CH_2)_i$—$SO_3M$, wherein 1 is 1, 2 or 3; or —$(CH_2)_n$—COOR, —$(CH_2)_n$—CONHR, —$(CH_2)_n$—OR, wherein i is an integer from 1 to 4, R is $C_1$-$C_3$ alkyl or has the same meaning as M; M represents hydrogen, Li, Na, K, Ca, Mg, ammonium, or ammonium which is mono-, di-, tri- or tetra-substituted by $C_1$-$C_4$ alkyl or $C_2$-$C_4$ hydroxyalkyl.

2. The fluorescent whitening agent composition according to claim 1, wherein $R_1$, $R_2$, $R_3$ and $R_4$ represent, independently of each other, $C_2$-$C_4$ hydroxyalkyl, or $C_1$-$C_4$ alkoxyalkyl.

3. The fluorescent whitening agent composition according to claim 1, wherein $R_1$, $R_2$, $R_3$ and $R_4$ represent a hydroxyethyl group.

4. The fluorescent whitening agent composition according to claim 1, wherein the composition comprises the fluorescent whitening agents of formula (1), formula (2) and formula (3).

5. The fluorescent whitening agent composition according to claim 1, wherein the fluorescent whitening agent of formula (1) is in an amount greater than 0 to 99 weight-%, the fluorescent whitening agent of formula (2) is in an amount greater than 0 to 99 weight-%, and the fluorescent whitening agent of formula (3) is in an amount of 0 to 99 weight-%, in each case based on 100 weight-% of the total amount of the fluorescent whitening agent.

6. The fluorescent whitening agent composition of claim 1, wherein the composition further comprises water in an amount of 20 to 90 weight-%, based on 100 weight-% of the total amount of the fluorescent whitening agents and water.

7. The fluorescent whitening agent composition according to claim 6, wherein the aqueous fluorescent whitening agent composition contains less than 30% by weight of other components.

* * * * *